(12) United States Patent
Kim

(10) Patent No.: US 10,194,737 B2
(45) Date of Patent: Feb. 5, 2019

(54) FINGERTIP TOOTHBRUSH FOR PET

(71) Applicant: Minjun Kim, Hanam-si (KR)

(72) Inventor: Minjun Kim, Hanam-si (KR)

( * ) Notice: Subject to any disclaimer, the term of this patent is extended or adjusted under 35 U.S.C. 154(b) by 94 days.

(21) Appl. No.: 15/594,633

(22) Filed: May 14, 2017

(65) Prior Publication Data

US 2017/0367297 A1    Dec. 28, 2017

(30) Foreign Application Priority Data

Jun. 27, 2016 (KR) ........................ 10-2016-0079862

(51) Int. Cl.
*A46B 5/04* (2006.01)
*A46B 13/02* (2006.01)
*A61D 5/00* (2006.01)
*A61C 17/34* (2006.01)
*A01K 13/00* (2006.01)
*A46B 9/04* (2006.01)

(52) U.S. Cl.
CPC .............. *A46B 5/04* (2013.01); *A01K 13/001* (2013.01); *A46B 9/04* (2013.01); *A46B 13/023* (2013.01); *A61C 17/3472* (2013.01); *A61C 17/3481* (2013.01); *A61D 5/00* (2013.01); *A46B 2200/1086* (2013.01)

(58) Field of Classification Search
CPC ........... A46B 5/04; A46B 13/00; A46B 13/02; A46B 13/023; A46B 2200/1066; A46B 2200/1086; A61D 5/00; A01K 13/00; A01K 13/001; A61C 17/22; A61C 17/32; A61C 17/34; A61C 17/3409; A61C 17/3445; A61C 17/3454; A61C 17/3463; A61C 17/3472; A61C 17/3481; A61H 13/00; A61H 7/00; A61H 7/003; A61H 7/005; A61H 23/02; A61H 23/0254; A61H 23/0263; A61H 23/0281
See application file for complete search history.

(56) References Cited

U.S. PATENT DOCUMENTS 7,124,462 B2    10/2006  Lee

FOREIGN PATENT DOCUMENTS

KR   20-1999-0017544 U    5/1999
KR       20-0401783 Y1   11/2005
KR         10-1476366 B1   12/2014

*Primary Examiner* — Mark Spisich
(74) *Attorney, Agent, or Firm* — Lee & Associates, LLC

(57) ABSTRACT

The present invention relates to a fingertip toothbrush for a pet, and more particularly, to a fingertip toothbrush for a pet that is configured to allow bristles to vibrate and reciprocally slide up and down, so that toothbrushing can be carefully and precisely achieved, which is effective in improving the teeth health of the pet.

2 Claims, 7 Drawing Sheets

FINGERTIP TOOTHBRUSH FOR PET

CROSS-REFERENCE TO RELATED APPLICATIONS

This patent application claims priority under 35 U.S.C. § 119 to Korean Patent Application No. 10-2016-0079862, filed on Jun. 27, 2016 in the Korean Intellectual Property Office, the disclosure of which is incorporated by reference herein in its entirety.

TECHNICAL FIELD

The present invention relates to a fingertip toothbrush for a pet, and more particularly, to a fingertip toothbrush for a pet that is configured to allow bristles to vibrate and reciprocally slide up and down, so that toothbrushing can be carefully and precisely achieved, which is effective in improving the teeth health of the pet.

BACKGROUND OF THE DISCLOSURE

A large family in a modern society has been transformed to a nuclear family, and further, the number of one-person households has been recently increased. Under such a social atmosphere, households of the owners who care for pets have been expanded.

A lot of cares for pets such as periodical washing, vaccination, and so on should be needed, but the cares for their teeth are not actually taken well.

If their teeth are not brushed, serious mouth odor and periodontitis may be easily generated. If the periodontitis is left untreated for a long period of time, it is developed to a gum disease, which undesirably causes decayed teeth, gum bleeding, and even teeth losing.

If bacteria living on the teeth enter their body, further, they have bad influences on their heart, lung, kidney and so on, which undesirably causes other diseases.

So as to solve such problems, recently, toothbrushes only for pet animals, especially, pet dogs have been proposed and purchased easily by users.

In a similar manner to toothbrushes for people, the toothbrushes for pets are provided with bristles formed on the end portion of a stick, but in case of small dogs, their mouth is small so that it is hard to brush their teeth carefully and precisely and damages on their gum may be further caused.

So as to avoid such problems, accordingly, a fingertip toothbrush for a pet has been proposed wherein the fingertip toothbrush is fitted to a user's finger to brush the pet's teeth, and in this case, the fingertip toothbrush has a cylindrical body made of a soft silicone material and a plurality of bristles formed on the end portion of the cylindrical body.

As the conventional fingertip toothbrush for the pet is fitted to the user's finger, the pet's teeth can be more perfectly brushed than the stick type toothbrush as mentioned above, but while the pet's teeth is being brushed, the user's finger should be kept carefully moving, thereby making it inconvenient to use.

SUMMARY OF THE INVENTION

Accordingly, the present invention has been made in view of the above-mentioned problems occurring in the prior art, and it is an object of the present invention to provide a fingertip toothbrush for a pet that is configured to allow bristles to reciprocally slide up and down or vibrate while the fingertip toothbrush is being used in the state of being fitted to a user's finger, so that the pet's teeth can be carefully and accurately brushed and since there is no need to move his or her finger during toothbrushing, it is very convenient to use.

To accomplish the above-mentioned object, according to the present invention, there is provided a fingertip toothbrush for a pet including: a cylindrical body open on one side thereof and having a slide groove formed on the outer peripheral surface thereof; a motion panel seated on the slide groove and having bristles formed on top thereof and a cam insertion groove formed on underside thereof; a motor having a shaft and fixed to the slide groove formed on the body; and a cam fastened to the shaft of the motor in such a manner as to be inserted into the cam insertion groove of the motion panel seated on the slide groove, wherein as the cam rotates by means of the driving of the motor, the motion panel reciprocally slides along the slide groove.

According to the present invention, desirably, water resistant films made of a soft material are formed on the edges of the slide groove and on the edges of the motion panel, thereby preventing the pet's saliva or water from being permeated into the slide groove and the motion panel.

According to the present invention, desirably, a vibrator is disposed at the interior of the motion panel to generate vibrations so that the motion panel slides up and down and vibrates.

According to the present invention, desirably, a switch is disposed at the end portion of the interior of the body, so that if a user's finger is fitted to the body, the finger touches the switch to automatically drive the motion panel.

According to the present invention, desirably, a control knob is disposed on the body to turn on/off the reciprocating sliding motion and vibrations of the motion panel, so that any one of the reciprocating sliding motion of the motion panel, the vibrations of the motion panel, and the vibrations and reciprocating sliding motion of the motion panel is selected.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
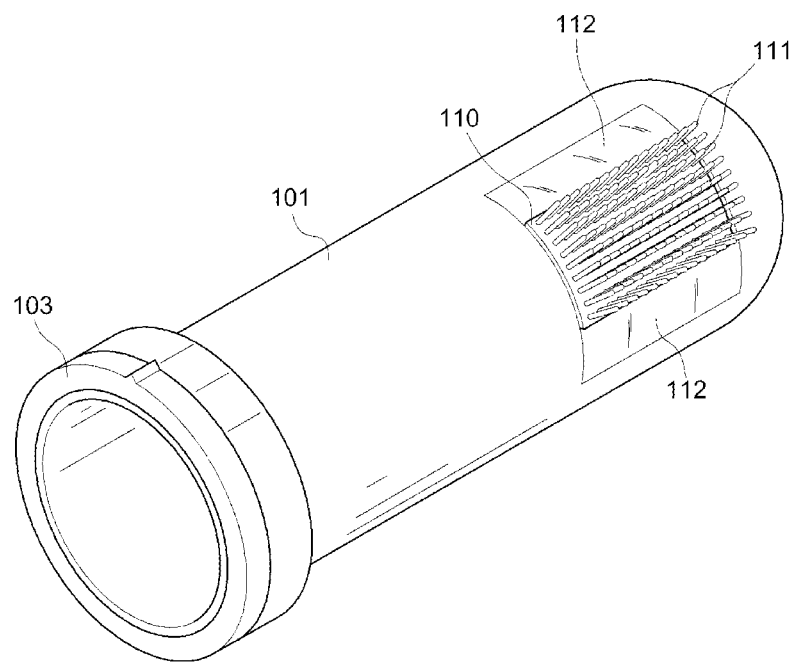
FIG. 1 is a perspective view showing a fingertip toothbrush for a pet according to the present invention.

Hereinafter, the present invention is disclosed with reference to the attached drawings wherein the corresponding parts in the embodiments of the present invention are indicated by corresponding reference numerals and the repeated explanation on the corresponding parts will be avoided.

In the description or claims, terms, such as "comprise", "include", or 'have", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

As shown in FIG. 1, a fingertip toothbrush for a pet according to the present invention includes a motion panel 110 disposed on the outer peripheral surface of one side of a cylindrical body 101 and having a plurality of bristles 111 formed thereon and an insertion hole formed on the other side of the cylindrical body 101 to insert a user's finger thereinto.

The fingertip toothbrush for a pet according to the present invention is configured wherein the motion panel 110 on which the bristles 111 are formed reciprocally slides up and down with respect to the body 101 or generates vibrations therefrom, thereby carefully brushing the pet's teeth and making the pet's gum healthy through gum massage.

Figure 2:
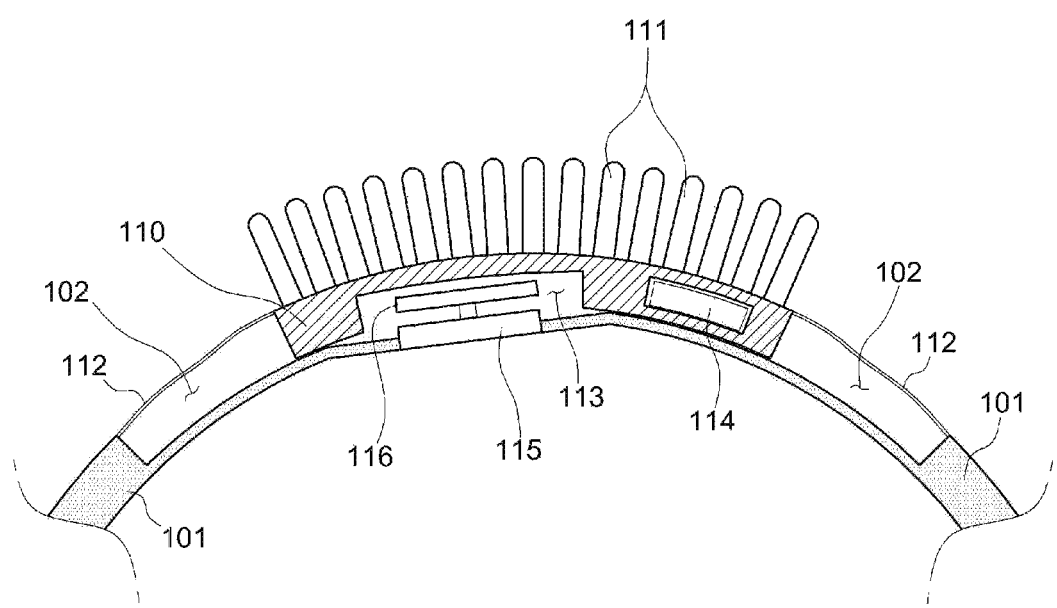
FIG. 2 is a sectional view showing a structure of a motion panel of the fingertip toothbrush for a pet according to the present invention.

The motion panel 110 is molded to a shape of a flat plate on which the bristles 111 are formed, and as shown in FIG. 2, the motion panel 110 is seated on a slide groove 102 formed on top of the body 101.

A cam 116 is disposed on the slide groove 102 in such a manner as to be rotated by means of the driving of a motor 115, and further, a cam insertion groove 113 is formed on the underside of the motion panel 110 so that when the motion panel 110 is seated on the slide groove 102, the cam 116 is inserted into the cam insertion groove 113 of the motion panel 110.

The motion panel 110 thus reciprocally slides up and down by means of the cam 116 rotating through the driving of the motor 115 fastened to the slide groove 102 of the body 101.

Figure 3:
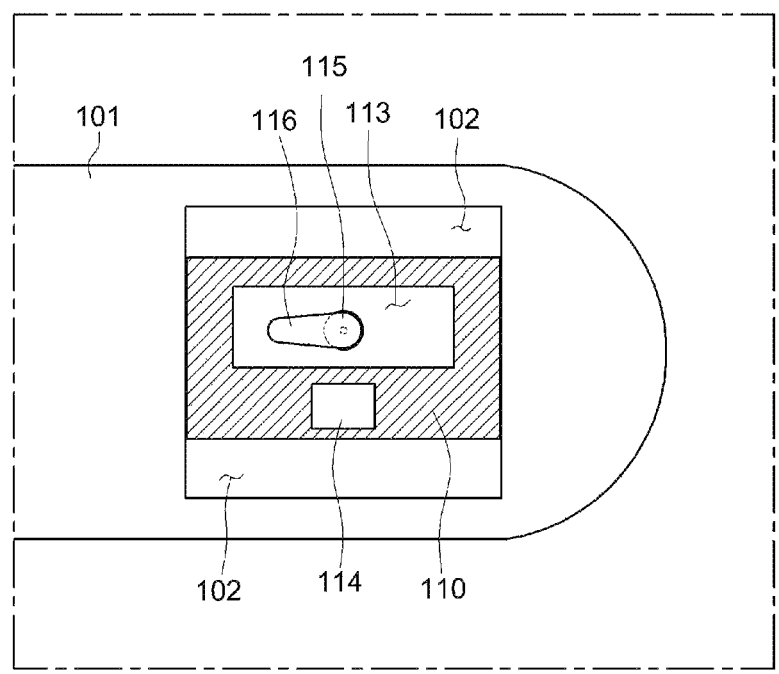
FIG. 3 is a view showing a location of a cam before power is supplied to a motor in the fingertip toothbrush for a pet according to the present invention.
Figure 4:
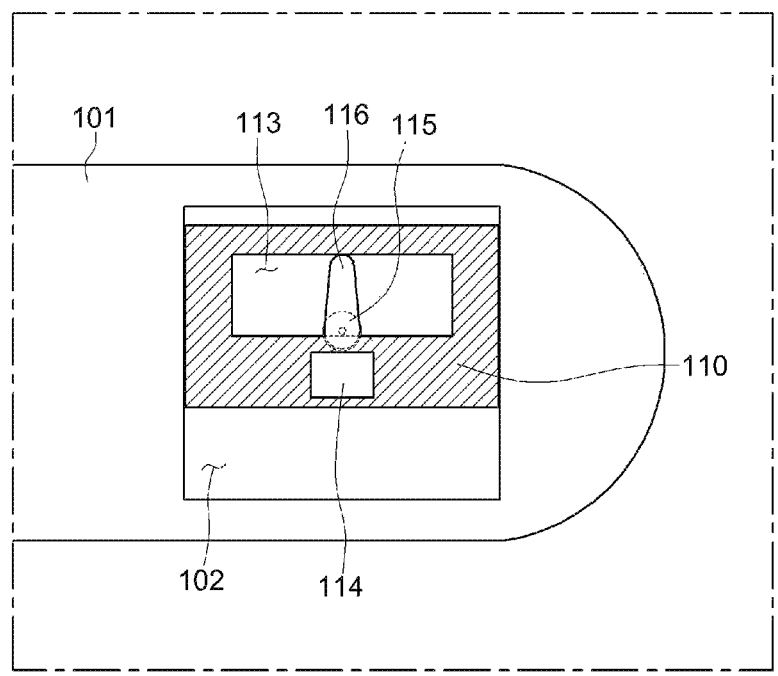
FIGS. 4 and 5 are views showing the up-and-down reciprocating sliding motions of the motion panel of the fingertip toothbrush for a pet according to the present invention through the rotation of the cam after the power is supplied to the motor.

As shown in FIG. 3, the cam insertion groove 113 is formed on the underside of the motion panel 110 in such a manner as to be extended in a longitudinal (axial) direction of the body 101, and in FIG. 4, hereinafter, the inner wall of the cam insertion groove 113 with which the cam 116 comes into contact is called 'upper inner wall', the inner wall of the cam insertion groove 113 facing the upper inner wall is called 'lower inner wall', and the inner walls of the cam insertion groove 113 formed on both sides of the cam 116 are called 'side inner walls'.

In the state where power is supplied to the motor 115, as shown in FIG. 3, the end portion of the cam 116 is located toward the side inner wall of the cam insertion groove 113 formed to the shape of the long hole, and at this time, the end portion of the cam 116 does not come into contact with one side inner wall.

If power is supplied to the motor 115 fixedly fastened to the body 101, on the other hand, the cam 116 fastened to the shaft of the motor 115 rotates, and as the cam 116 rotates, the end portion of the cam 116 comes into contact with the upper inner wall of the cam insertion groove 113. In this state, the cam 116 rotates, and as shown in FIG. 4, the cam 116 moves up the motion panel 110 up to the top portion of the slide groove 102.

Figure 5:
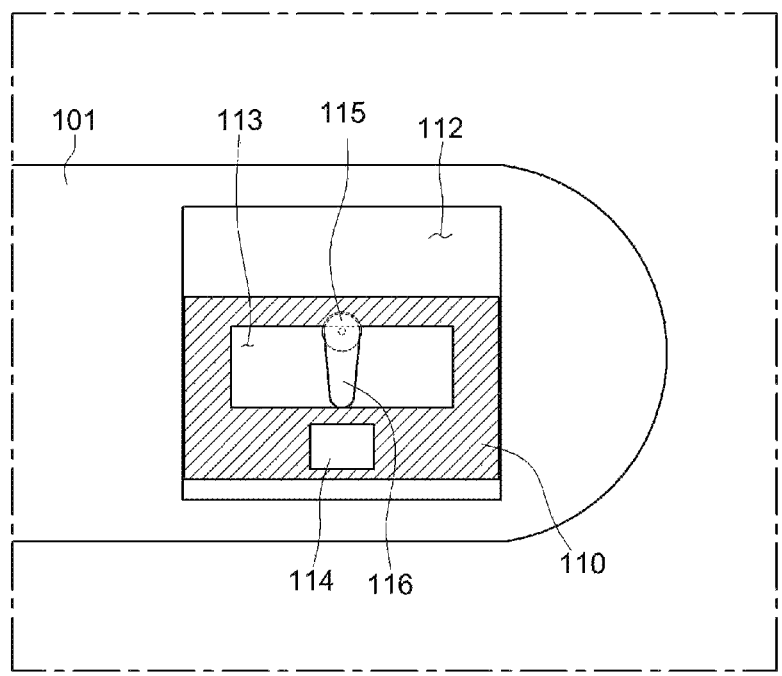

If the cam 116 is kept rotating, further, the end portion of the cam 116 comes into contact with the lower inner wall of the cam insertion groove 113. In this state, the cam 116 rotates, and as shown in FIG. 5, the cam 116 moves down the motion panel 110 up to the bottom portion of the slide groove 102.

As the above-mentioned processes are repeatedly carried out through the driving of the motor 115, the motion panel 110 reciprocally slides up and down along the slide groove 102 of the body 101.

Figure 7:
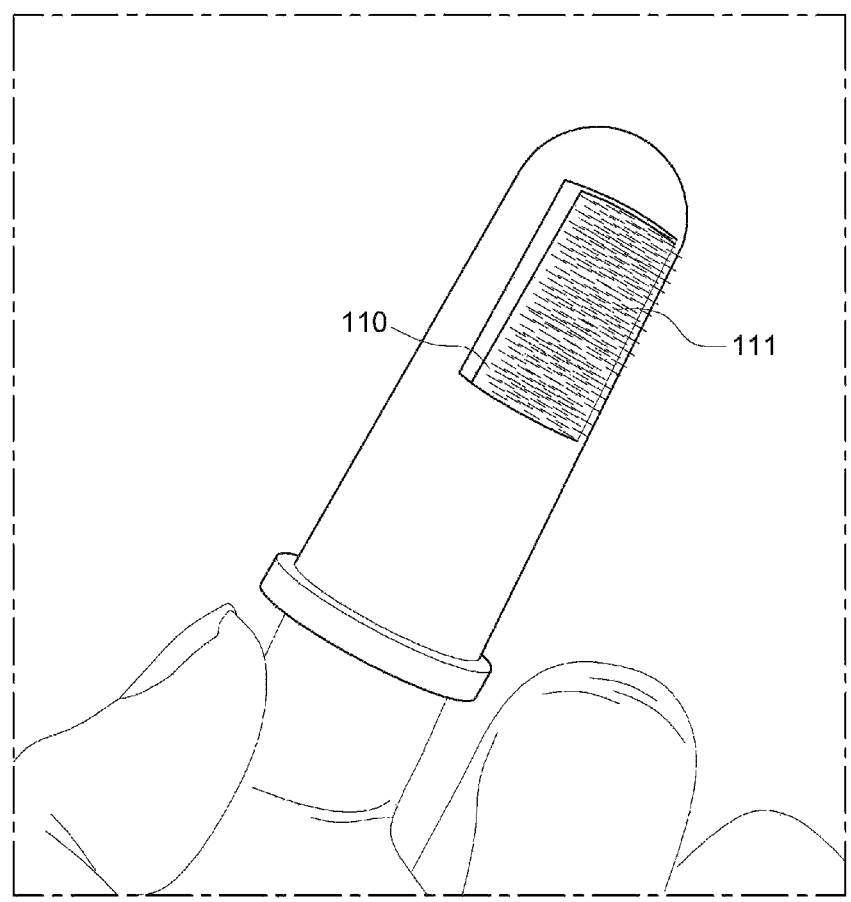
FIG. 7 is a perspective view showing a state wherein the fingertip toothbrush for a pet according to the present invention is worn on a user's finger.

Accordingly, as shown in FIG. 7, if the bristles 111 just come into contact with the pet's teeth in the state where the fingertip toothbrush according to the present invention is fitted to the user's finger, the motion panel 110 reciprocally slides up and down to allow the bristles 111 formed thereon to carefully brush the pet's teeth.

Further, as shown in FIGS. 2 to 5, a vibrator 114 is located at the interior of the motion panel 110 to generate vibrations through the supply of power.

The vibrator 114 is fixedly fastened to the interior of the motion panel 110, and if the vibrator 114 is driven through the supply of power, the vibrations generated from the vibrator 114 are transferred to the bristles 111 formed on the motion panel 110.

If the bristles 111 are vibrated, the pet's teeth can be finely and carefully brushed, and further, vibration stimulations can be applied to the pet's gum, thereby making the gum healthy.

The vibrator 114 can be operated at the same time when the motion panel 110 reciprocally slides up and down, and otherwise, it can be operated solely even when the motion panel 110 does not reciprocally slide up and down.

The vibrator 114 is a well known technology, and therefore, a detailed explanation on the internal structure of the vibrator 114 will be avoided for the brevity of the description.

Figure 6:
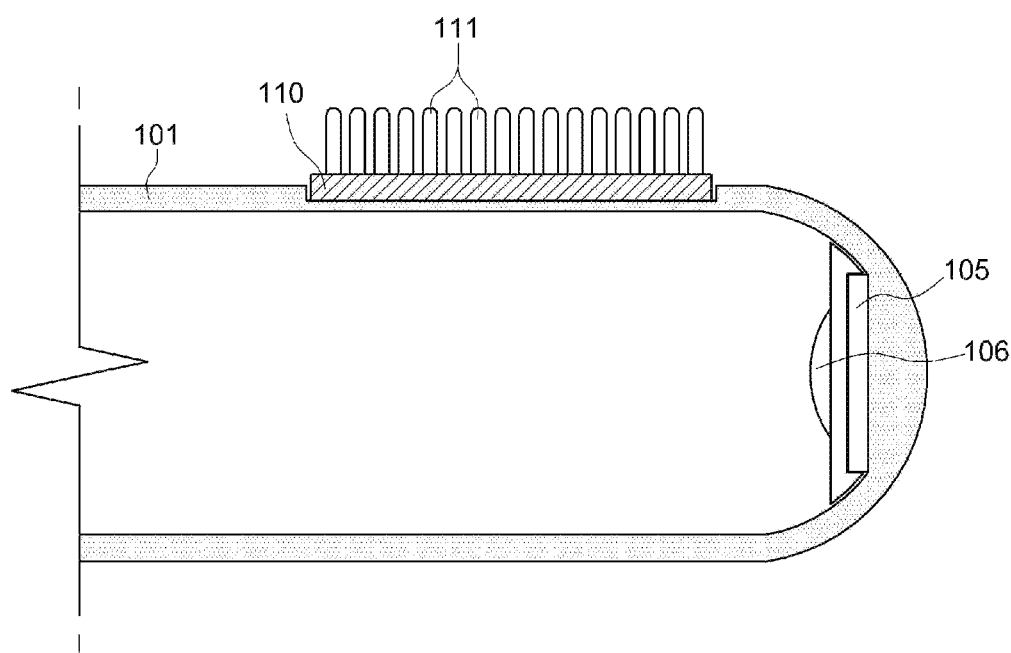
FIG. 6 is a side view showing a driving switch disposed at the interior of the fingertip toothbrush for a pet according to the present invention.

The motor 115 adapted to allow the motion panel 110 to reciprocally slide up and down and a switch adapted to turn the vibrator 114 on/off may be configured to a variety of forms. According to the present invention, as shown in FIG. 1, a control knob 103 is disposed at the insertion hole of the fingertip toothbrush, and as shown in FIG. 6, a switch 106 and a battery 105 supplying power to the switch 106 are disposed at the interior of the fingertip toothbrush.

According to the present invention, the reciprocating sliding motions and vibrations of the motion panel 110 can be turned on/off through the control knob 103 and the switch 106.

If the user's finger is inserted into the fingertip toothbrush according to the present invention, his or her finger comes into contact with the switch 106 disposed at the interior of the body 101 to allow the motion panel 110 to reciprocally slide in an automatic manner, so that the fingertip toothbrush according to the present invention can be conveniently used, without any separate switching manipulation.

As the control knob 103 as shown in FIG. 1 is turned, the vibrator 114 disposed at the interior of the motion panel 110 is turned on/off, and the reciprocating sliding motion of the motion panel 110 is turned on/off so as to drive the vibrator 114 solely.

According to the present invention, the control knob 103 is configured to the form of a three-stage switch comprising three modes such as 'vibrator OFF', 'vibrator ON', and 'motion panel reciprocating motion OFF and vibrator ON'.

In the 'vibrator OFF' mode of the control knob 103, only the reciprocating sliding motion of the motion panel 110 is generated, in the 'vibrator ON' mode of the control knob 103, the reciprocating sliding motion of the motion panel 110 and the vibrations of the vibrator 114 are at the same time generated, and in the 'motion panel reciprocating motion OFF and vibrator ON' mode of the control knob 103, the reciprocating sliding motion of the motion panel 110 stops and only the vibrator 114 is driven even if the user's finger comes into contact with the switch 106 disposed at the interior of the body 101.

At this time, the manipulation of the control knob 103 is desirably carried out only when the fingertip toothbrush is worn on the user's finger, that is, when his or her finger comes into contact with the switch 106 disposed at the interior of the body 101.

While the fingertip toothbrush is being used, further, the internal electric parts like the motor 115 may be malfunctioned by the pet's saliva or water introduced into the fingertip toothbrush, and so as to prevent such malfunction from occurring, as shown in FIG. 2, water resistant films 112 are formed on the edges of the motion panel 110 and on the edges of the slide groove 102 of the body 101 to seal them, so that no water cannot be desirably permeated into them.

The water resistant films 112 are made of a tough material having excellent softness like silicone, so that while the motion panel 110 reciprocally slides, the water resistant films 112 are not folded or extended at all, thereby preventing their damage or breakage.

As mentioned above, if the fingertip toothbrush for a pet according to the present invention is fitted to the user's finger, the motion panel 110 reciprocally slides up and down in the automatic manner or generates vibrations, so that the pet's teeth can be carefully and accurately brushed, and since there is no need to move his or her finger during toothbrushing, further, just the position of the toothbrushing is fixed, so that it is very convenient to use.

The technical idea of the present invention has been explained with reference to the above-mentioned embodiment of the present invention.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A fingertip toothbrush for a pet, comprising:
   a cylindrical body open on one side and having a slide groove formed on an outer peripheral surface thereof;
   a motion panel seated on the slide groove and having bristles formed on top thereof and a cam insertion groove formed on underside thereof;
   a motor having a shaft and fixed to the slide groove formed on the body;
   a cam fastened to the shaft of the motor L in such a manner as to be inserted into the cam insertion groove of the motion panel seated on the slide groove;
   a vibrator disposed at the interior of the motion panel to generate vibrations;
   a control knob disposed on the body to selectively drive the motor and the vibrator; and
   a switch disposed at an end portion of the interior of the body opposite the open side,
   wherein the motion panel, the motor, the vibrator, the switch and the control knob are formed integrally with the body to conduct one-handed manipulation;
   as the cam rotates by the driving of the motor, the motion panel reciprocally slides along the slide groove and the motion panel vibrates through the driving of the vibrator;
   at least one of the reciprocating sliding motion and vibrations of the motion panel is conducted through the manipulation of the control knob;
   the control knob is configured to have three modes including a 'vibrator OFF' mode, a 'vibrator ON' mode, and a 'motion panel reciprocating motion OFF and vibrator ON' mode, only a reciprocating sliding motion of the motion panel is generated in the 'vibrator OFF' mode of the control knob, the reciprocating sliding motion of the motion panel and vibrations of the vibrator are simultaneously generated in the 'vibrator ON' mode, and the reciprocating sliding motion of the motion panel stops and the vibrator is driven in the 'motion panel reciprocating motion OFF and vibrator ON' mode;
   the control knob is disposed at a ring-shaped insertion hole formed on the open one side of the body;
   if the user's finger passes through the control knob to touch the switch, the motion panel is driven according to the manipulation of the control knob; and
   the operation of the corresponding mode to the manipulation of the control knob is conducted under the condition where the switch is touched.

2. The fingertip toothbrush for a pet according to claim 1, wherein water resistant films made of a soft material are formed on the edges of the slide groove and on the edges of the motion panel.

* * * * *